United States Patent [19]
Nickerson

[11] Patent Number: 5,716,525
[45] Date of Patent: Feb. 10, 1998

[54] PORTABLE EXTRACTION INSTRUMENT

[75] Inventor: Mark A. Nickerson, Landenberg, Pa.

[73] Assignee: Hewlett-Packard Co., Palo Alto, Calif.

[21] Appl. No.: 624,334

[22] Filed: Apr. 3, 1996

Related U.S. Application Data

[62] Division of Ser. No. 373,730, Jan. 17, 1995, Pat. No. 5,549,819.

[51] Int. Cl.$^6$ ................................................ B01D 15/08
[52] U.S. Cl. ........................ 210/634; 210/656; 210/659; 95/82
[58] Field of Search .................... 210/634, 656, 210/659, 181, 241, 198.2, 511, 541; 422/255, 261, 285; 95/82; 96/101, 105, 107

[56] References Cited

U.S. PATENT DOCUMENTS

| | | | |
|---|---|---|---|
| 4,424,131 | 1/1984 | Baird | 210/634 |
| 5,013,443 | 5/1991 | Higashidate | 210/634 |
| 5,087,360 | 2/1992 | Wright | 210/634 |
| 5,094,741 | 3/1992 | Frank | 210/634 |
| 5,133,859 | 7/1992 | Frank | 210/198.2 |
| 5,147,538 | 9/1992 | Wright | 210/634 |
| 5,205,987 | 4/1993 | Ashraf-Khorassani | 210/198.2 |
| 5,240,603 | 8/1993 | Frank | 210/198.2 |
| 5,322,626 | 6/1994 | Frank | 210/634 |
| 5,356,538 | 10/1994 | Wai | 210/511 |
| 5,472,612 | 12/1995 | Maxwell | 96/105 |

*Primary Examiner*—Ernest G. Therkorn
*Attorney, Agent, or Firm*—Mark Z. Dudley

[57] ABSTRACT

Methods and apparatus for extracting an analyte from a sample using a field-portable extraction instrument. The preferred embodiment of the extraction instrument includes an extraction fluid source, a sample container, a valve element, a nozzle, and a collection trap vessel. The methods of the present invention include the steps of inserting the sample into the sample container, attaching the sample container to the instrument, and providing a quantity of pressurized extraction fluid from the pressurized extraction fluid source into the sample container to initiate the extraction process. Extraction is facilitated by directing the extraction fluid into the sample at a rapid flow rate such that the sample and extraction fluid are vigorously mixed and a sample/solvent mixture is created. The valve element is then operated to isolate the extraction fluid source and to fully close the sample container. As an optional step, heat may be applied to the closed sample container to create conditions for effecting supercritical fluid extraction. The valve element is then operated to direct a fluid/constituent mixture from the sample container section to the collection trap vessel. The analyte of interest that is present in the fluid/constituent mixture is thereby trapped.

4 Claims, 5 Drawing Sheets

PORTABLE EXTRACTION INSTRUMENT

This is a divisional of application Ser. No. 08/373,730 filed on Jan. 17, 1995, now U.S. Pat. No. 5,549,819.

FIELD OF THE INVENTION

The present invention relates generally to methods and apparatus for extracting one or more constituent components from a sample and, more particularly, to a field-portable method and apparatus for extraction of an analyte of interest prior to chemical analysis.

BACKGROUND OF THE INVENTION

A constituent component of interest in a solid or liquid sample may be extracted by use of laboratory-based techniques known in the sample preparation arts. One useful extraction process is solvation, whereby application of a solvent fluid to the sample causes constituent components to be dissolved in the solvent. The constituent component of interest in such an extraction process may be either the isolated material (known as the extract) or the material remaining in the sample after extraction (known as the raffinate). Another process of extraction may be achieved by volatilization, wherein the constituent components of interest are swept or otherwise released from the sample by the influence of a vapor pressure differential.

However, the aforementioned extraction processes heretofore have been difficult to perform in a simple, manually-operable instrument that is suited for use not only in the laboratory, but more importantly, in a location outside of the laboratory. Such an instrument would be considered field-portable and would be useful outside of the laboratory for performing remote sample analysis or field monitoring.

A need also exists to simplify the aforementioned extraction processes, regardless of whether they may be employed in the field or in the laboratory, because conventional extraction procedures are expensive, labor-intensive, equipment-intensive, and time-consuming. In particular, it would be highly desirable for effecting a volatilization process in a field-portable extraction instrument so as to obtain an extract or raffinate in a form that is quickly and easily introduced into a field-portable analytical instrument. Alternatively, there is a need for providing such extraction in the field whereby the extract or raffinate is produced in a container or vessel that is easily transportable to an analytical instrument that is not portable and which may be situated nearby, such as in a vehicle, or at a location quite distant from the monitored site, such as in a laboratory.

A field-portable extraction system that employs an extraction fluid in the form of a solvent fluid at a an elevated pressure (i.e., above atmospheric pressure) is also desirable. For example, supercritical fluids have been used as solvents in extraction instruments. When compared to typical liquid solvents, the supercritical fluid has particular transport properties that allow enhanced mass transport within complex sample matrices, such as coal, plant tissue, or animal tissue. These attributes make supercritical fluids especially attractive for performing sample extraction in the field. However, the requisite pressure is conventionally achieved by use of high-pressure pumps and related apparatus that are typically not suited for portable use. This problem is especially difficult in constructing extraction systems that operate with solvent fluids at supercritical conditions, as well as in extraction systems that use solvent fluids at near-critical conditions.

It would be desirable and of considerable advantage to provide a sample extraction technique that differs from that employed in the traditional laboratory-based extraction, so as to be effective in the field, even if such a new technique provides less-than-perfect extraction.

SUMMARY OF THE INVENTION

The present invention provides a method and apparatus for field-portable sample extraction which extracts one or more analytes from a complex sample, using an extraction fluid such as carbon dioxide, and deposits the resulting analyte in a user-chosen collection trap vessel. The collection trap vessel is directly compatible with automatic injection systems of other analytical instruments (e.g., liquid chromatograph, gas chromatograph, supercritical fluid chromatograph) and is especially suited for use with a field-portable analytical instrument.

Accordingly, methods of extracting an analyte from a sample using a portable extraction instrument are disclosed. The preferred embodiment of the portable extraction instrument includes an extraction fluid source, a sample container, a valve element, and an analyte trap subassembly having a collection trap vessel. The methods of the present invention include the steps of inserting the sample into the sample container, attaching the sample container to the instrument, and providing a quantity of pressurized extraction fluid from the pressurized extraction fluid source into the sample container to initiate the extraction process. Extraction is facilitated by directing the extraction fluid into the sample at a rapid flow rate such that the sample and extraction fluid are vigorously mixed and a sample/fluid mixture is created. The extraction fluid flow is self-limited when the pressure in the sample container is equalized with the pressure in the extraction fluid source. The valve element is then operated to isolate the extraction fluid source and to contain the sample/fluid mixture in the sample container. As an optional step, heat may be applied to the sample container to create conditions for effecting supercritical fluid extraction. After a predetermined time, one or more constituents of interest are provided in a fluid/constituent mixture. The valve element is then operated to direct the fluid/constituent mixture, still under pressure, from the sample container section to the analyte trap subassembly. The analyte(s) of interest that are present in the fluid/constituent mixture are then trapped (separated from the fluid/constituent mixture) as the pressurized fluid/constituent mixture flows through the collection trap vessel.

The present invention may also be adapted in certain embodiments to provide a rinse operation whereby the extraction instrument, and in particular the valve element, may be rinsed with solvent in order to prevent occlusion or other problems associated with the accumulation of particulate matter, or to rinse the collection vessel so as to output the analyte of interest in the rinse flow.

The contemplated portable extraction instrument may be constructed to function as a lightweight, rugged, pocket-sized, field-serviceable, and easily-manipulated device. It may be constructed as a hand-held instrument that can be used in the field without reliance upon the typical attributes of a laboratory (such as unlimited electrical power, extensive supplies, and a clean working environment). In the field environment, where there can be a need for performing a great number of extractions in a short time, the contemplated instrument may be operated in a quick and easy fashion for inputting the sample, performing the extraction, and trapping the analyte of interest.

There is also the problem that the instrument operator may be working in an adverse or hazardous environment, and may be wearing gloves, a mask, and other protective clothing or apparatus. The contemplated instrument is easily manipulated under such conditions.

The contemplated portable extraction instrument has the ability to accept differing quantities and types of samples, and is useable without major modifications when such differing types of samples are to be subjected to extraction. The portable extraction instrument is able to accept differing quantities and types of extraction fluids, and is fully operable without modifications when differing extraction fluids are employed.

Another attribute of the portable extraction instrument is the use of portable, standardized parts for use as the sample containers and collection trap vessels. Such parts may employ machine-readable indicia for automated identification and retrieval; or be manufactured in quantities so as to be inexpensive; or be wholly or partially composed of disposable components, such as a liner fitted in the sample container. The user may thus collect a large number of samples and perform respective extractions in a simple and cost-effective manner. These attributes are especially beneficial when the portable extraction instrument is used for the type of repetitive extractions that are typically performed in a field monitoring operation.

Whereas the contemplated extraction instrument may be usefully deployed in the field, it nonetheless is amenable to use with any integrated analytical system, whether that system is also field-portable, located in a vehicle, or maintained in a laboratory. For example, the contemplated extraction instrument employs sample containers and collection trap vessels that, having been used in the extraction process, can be collected in a less-than-orderly fashion into a basket, bag, or the like. Later, perhaps in a laboratory, the sample containers may be retrieved for disposal or recycling, and the collection trap vessels may be retrieved for performing an analysis of the extracted analyte(s).

DETAILED DESCRIPTION OF THE PREFERRED EMBODIMENTS

In accordance with a first aspect of the present invention, a user may initiate first or second preferred extraction processes for sample extraction by use of a preferred embodiment of a portable extraction instrument. In a first preferred extraction process based on solvation, an extraction fluid in the form of a solvent fluid is employed in the extraction instrument in the following steps: (1) inserting a sample in a sample container and attaching the sample container to the extraction instrument; (2) withdrawing a quantity of pressurized extraction fluid from an extraction fluid source; (3) directing the withdrawn quantity of extraction fluid through a first flow path in a valve element at a predetermined flow rate into the sample container, in order to cause the extraction fluid and sample to mix and form a sample/fluid mixture; (4) arresting the extraction fluid flow and initiating a selectable time period for achieving solvation of one or more constituents of interest, thus providing a fluid/constituent mixture; (5) (optionally) including an elevated temperature in the sample/fluid mixture while the sample/fluid mixture is contained in the sample container so as to create a supercritical or near-supercritical condition and thus facilitate extraction; and (6) when the time period has elapsed, directing the fluid/constituent mixture through a second flow path in the valve element and into a collection trap vessel. The analyte of interest that is present in the fluid/constituent mixture is then trapped while the remainder of the fluid/constituent mixture is allowed to escape the collection trap vessel through a vent.

In a second preferred extraction process based on volatilization, an extraction fluid in the form of a volatile fluid is employed in the portable extraction instrument in the following steps: (1) inserting a sample in a sample container and attaching the sample container to the extraction instrument; (2) withdrawing a quantity of extraction fluid from a pressurized extraction fluid source; (3) directing the withdrawn quantity of extraction fluid through a first flow path in a valve element into the sample container, in order to cause the volatile fluid and sample to mix and form a sample/fluid mixture; (4) arresting the extraction fluid flow and initiating a selectable time period for achieving volatilization of one or more sample constituents of interest, thus providing a fluid/constituent mixture, preferably in a headspace within the sample container; and (5) withdrawing the fluid/constituent mixture from the headspace through a second flow path in the valve element and into a collection trap vessel for trapping the analyte of interest.

Figure 1:
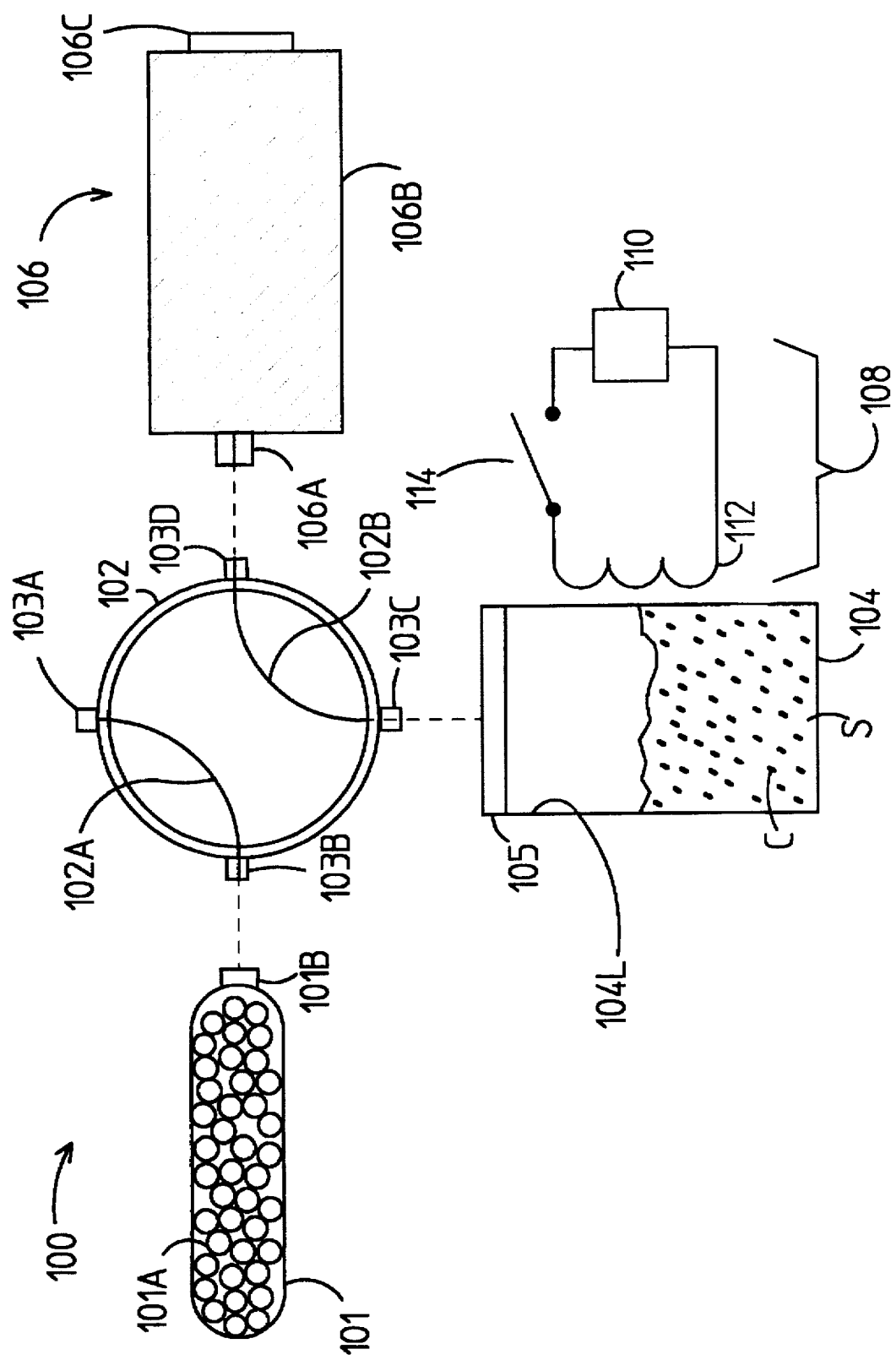
FIG. 1 is a simplified schematic representation of a portable extraction instrument made in accordance with the present invention and having been loaded with a sample that is to be subjected to an extraction process.

As shown in FIG. 1, a preferred embodiment of a portable extraction instrument 100 may be constructed according to the present invention. The extraction instrument 100 includes: a miniature extraction fluid source 101; a valve element 102 that incorporates first and second flow paths 102A, 102B; a sample container 104 with a detachable cap 105 and optional, removable liner 104L; an analyte trap subassembly 106; and an optional heating unit 108. For effecting solvation, the pressurized extraction fluid 101A is preferably a predetermined quantity of liquefied carbon dioxide that is contained in the extraction fluid source 101.

The preferred embodiment of the extraction fluid source 101 is a miniature gas cylinder pre-loaded with an appropriate extraction fluid. The preferred embodiment of the miniature gas cylinder is substantially smaller than the cylinders typically employed as a conventional gas source in the laboratory, and has dimensions of approximately 1.5 centimeters (cm.) width by 5 cm. length up to approximately 5 cm. width by 30 cm. length. One example of a miniature gas cylinder is commercially available as a lecture bottle from Air Products, Inc.

The valve element 102 is preferably a rotary valve that may be manipulated or otherwise set to one of several positions for switching or redirecting fluid flow between certain ports on the valve. However, other types of valve elements may be employed, such as linear valves, to accomplish the fluid flow switching function.

Before the extraction process is initiated, the several portions of the extraction instrument 100 illustrated in FIG.

1 are assembled to form a unit. However, for clarity of illustration, the extraction fluid source 101, sample container 104 (with cap 105 attached), and the analyte trap subassembly are shown displaced from second, third and fourth valve element ports 103B, 103C, 103D. The dashed lines illustrate the fluid tight connections that may be realized on complete assembly of the various parts. For the purposes of effecting the extraction process contemplated in the present invention, the first valve element port 103A is typically maintained in a closed state. However, it is contemplated that it may be opened to provide a fluid path to or from the extraction fluid source 101 for recharging, pressure checking, bleeding, cleaning, etc. of the extraction fluid source 101. The extraction fluid source 101 attaches to the valve element 102 by attaching the outlet 101B to the second valve element port 103B; the cap 105 attaches to the third valve element port 103C; and the analyte trap subassembly 106 attaches to the valve element 106 by attaching the nozzle 106A to the fourth valve element port 103D.

Optionally, an additional portion of the extraction instrument 100 may include apparatus for effecting a controlled application of heat to the contents of the sample container 104. A suitable heating unit 108 is illustrated as including a power source 110, a heating element 112, and a switch 114. The switch 114 is kept open to prevent application of power from the power source 110 to the heating element 112 until such heating is necessary. Closure of the switch 114 causes current to flow through the heating element 112. Heat may be generated by the heating element 112 according to known resistive, thermoelectric, thermochemical, microwave, or other heating techniques and applied to the contents of the sample container 104.

In the illustrated embodiment, the sample container 104 holds a sample (S) which contains one or more analytes (C) that are to be isolated by extraction. The preferred form of sample (S) comprises powdered solid, or liquid, samples. It is also contemplated that one may introduce small quantities (i.e., microliter to milliliters in volume) of a liquid sample by distributing the liquid sample upon solid supports such as filter paper, adsorbents, or powders. Similarly, semi-solids such as fats and creams can be input. Typically, the analytes (C) are chemical or elemental components of the sample (S) and are therefore not visible. However, for the purposes of illustrating the invention, the analytes (C) are symbolically illustrated as being distinguishable within the bulk of the sample (S).

The sample container 104 is preferably constructed to allow the operator to detach the sample container 104 from the cap 105. The operator may then freely manipulate the sample container 104 such that a sample (S) may be dropped, injected, scooped, or otherwise collected in the sample container 104. By returning the sample container 104 onto the cap 105, with subsequent achievement of a gas-tight seal made between the cap 105 and sample container 104, the cap 105 may then be attached to the third valve element port 103C. The contemplated design of the interface of the sample container 104 and the cap 105 may be selected as known in the art to effect the requisite seal while permitting various sizes and shapes of sample containers 104 to be accommodated on the cap 105.

An analyte trap subassembly 106 preferably includes a nozzle 106A, a collection trap vessel 106B, and an output fitting 106C. The interior of the collection trap vessel 106 is equipped with a quantity of trapping material suitable for trapping the analyte of interest. The output fitting 106C is open such that it may act as a vent to the ambient atmosphere. The internal temperature and pressure of the sample container 104, second flow path 102B, and the collection trap vessel 106B are therefore at ambient conditions. To minimize the failure of the analyte trap subassembly 214 due to particulates, a filter is preferably provided in the cap 105 so as to prevent the flow of particulates from the sample container 104 downstream to the analyte trap subassembly 106.

To perform an extraction, the sample (S) is first provided in the sample container 104, the parts of the extraction instrument 100 are assembled (if not done already), and the valve element 101 is operated in several successive positions until the analyte of interest is captured in the collection trap vessel 106B. As illustrated in FIG. 1, a first position may be achieved wherein the first flow path 102A is positioned to communicate with the outlet 101B of the extraction fluid source 101 and the first valve element port 103A on the valve element 102. Also as illustrated, the first position causes a second flow path 102B to be located to communicate with the interior of a sample container 104 by way of a passageway in a detachable cap 105. The second flow path 102B is also located in communication with the analyte trap subassembly 106.

Figure 2:
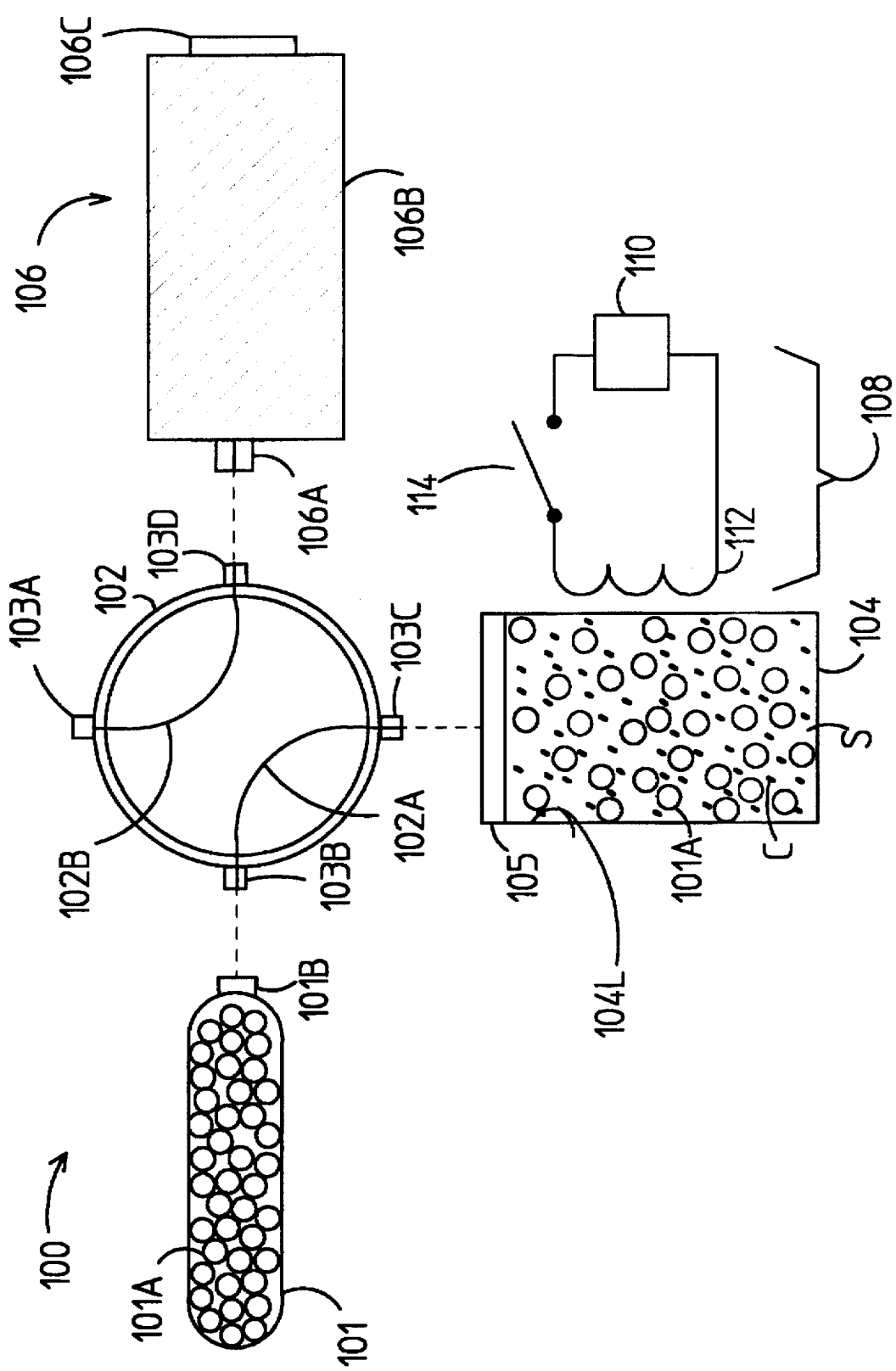
FIG. 2 depicts another simplified schematic representation of the embodiment of FIG. 1 during the initiation of the extraction process.

As illustrated in FIG. 2, rotation of the valve element 102 by a quarter-turn to a second position causes a quantity of the pressurized extraction fluid to flow along the first flow path 102A and through the cap 105 into the interior of the sample container 104. The extraction fluid is pressurized such that the fluid rushes into the sample container 104 until the internal pressure $P_{sc}$ of the sample container rises from ambient (atmospheric) pressure to an elevated pressure that is substantially equal to the internal pressure $P_{sf}$ of the extraction fluid source 101. Thus, immediately after such manipulation of the valve element 102 from the first to the second position, the interior of the sample container 104 experiences a turbulent and effective mixing of the extraction fluid 101A and the sample (S) until the pressures equalize. The resulting mixture of the extraction fluid 101A and the sample (S) will be described hereafter as the sample/fluid mixture.

Figure 3:
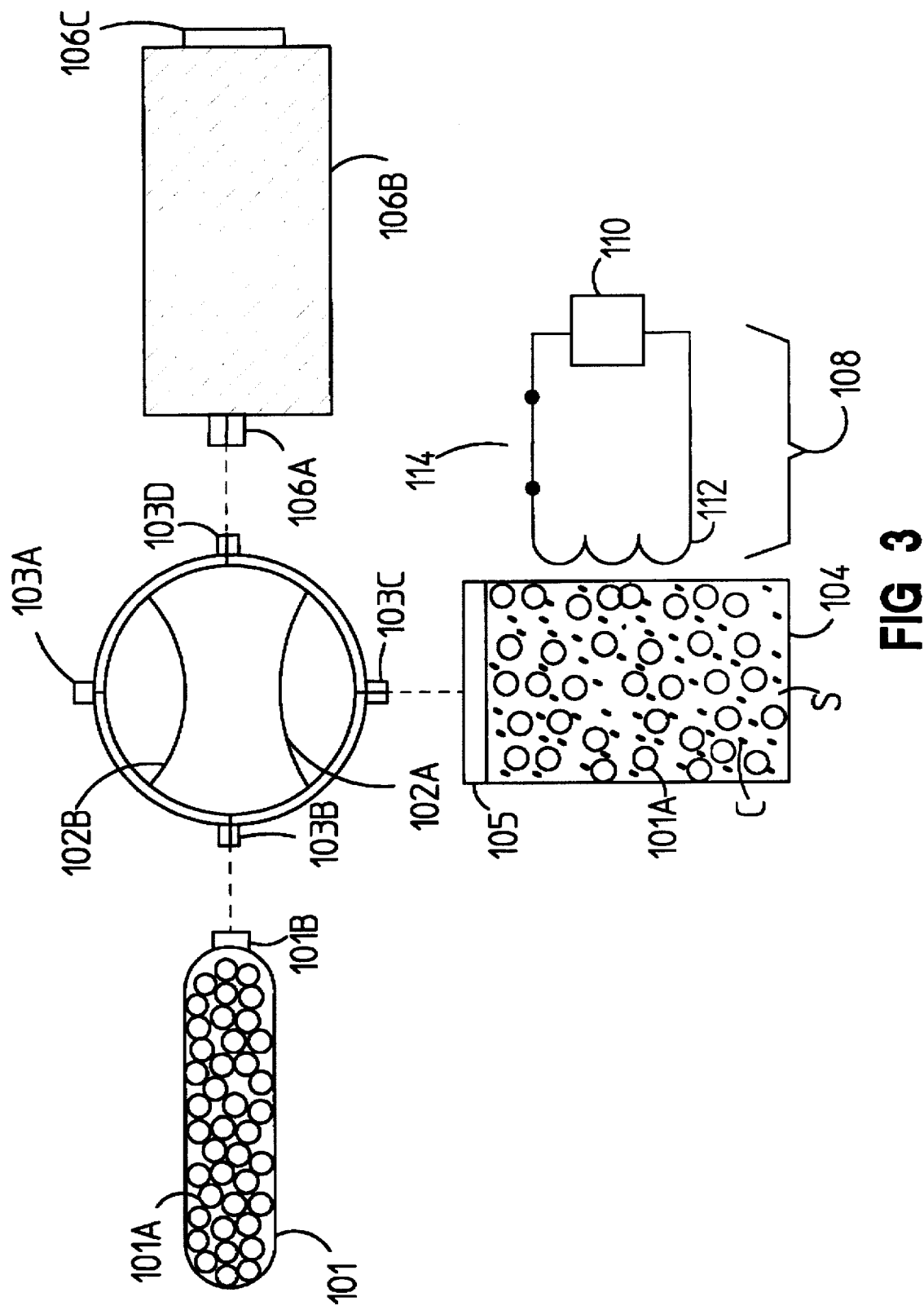
FIG. 3 depicts another simplified schematic representation of the embodiment of FIG. 1 during an optional application of heat to enhance the extraction process.

As illustrated in FIG. 3, a third position of the valve element 102 may be effected by rotating approximately an additional one-eighth turn so as to offset the first flow path 102A from communication with the sample container 104 and thus close the sample container 104. As a result of the conditions achieved in the configuration of the extraction instrument as illustrated in FIGS. 2 and 3, the sample/solvent mixture is effected to such an extent that one or more constituents of interest are dissolved in the solvent. For the purposes of description, the dissolved constituents will be considered to create a fluid/constituent mixture.

An optional heating step may be employed in some applications to provide the fluid/constituent mixture more effectively or more completely. To do so, the heating unit 108 may be activated for a short time period to heat the sample/solvent mixture to supercritical, near-supercritical, or critical conditions. With use of appropriate extraction fluids, the parameter of solvent power (solvency), which is a function of pressure and temperature, is directly related to the density of the extraction fluid; therefore, solvent power is adjustable and selectable by regulating the temperature of the sample/fluid mixture. It is preferable to operate the heating unit 108 to attain a selected operating density and temperature of the quantity of the extraction fluid 101 present in the sample/solvent mixture. The heating unit may then be deactivated by opening the switch 114. Depending upon the application and the particular conditions attained in the sample container, the heated sample/fluid mixture may then be considered ready for the next (fourth) position of the extraction process, or a delay is provided to allow the sample/solvent mixture to cool. In any event, the pressure in the sample container 104 remains at an elevated pressure in comparison to atmospheric pressure.

Figure 4:
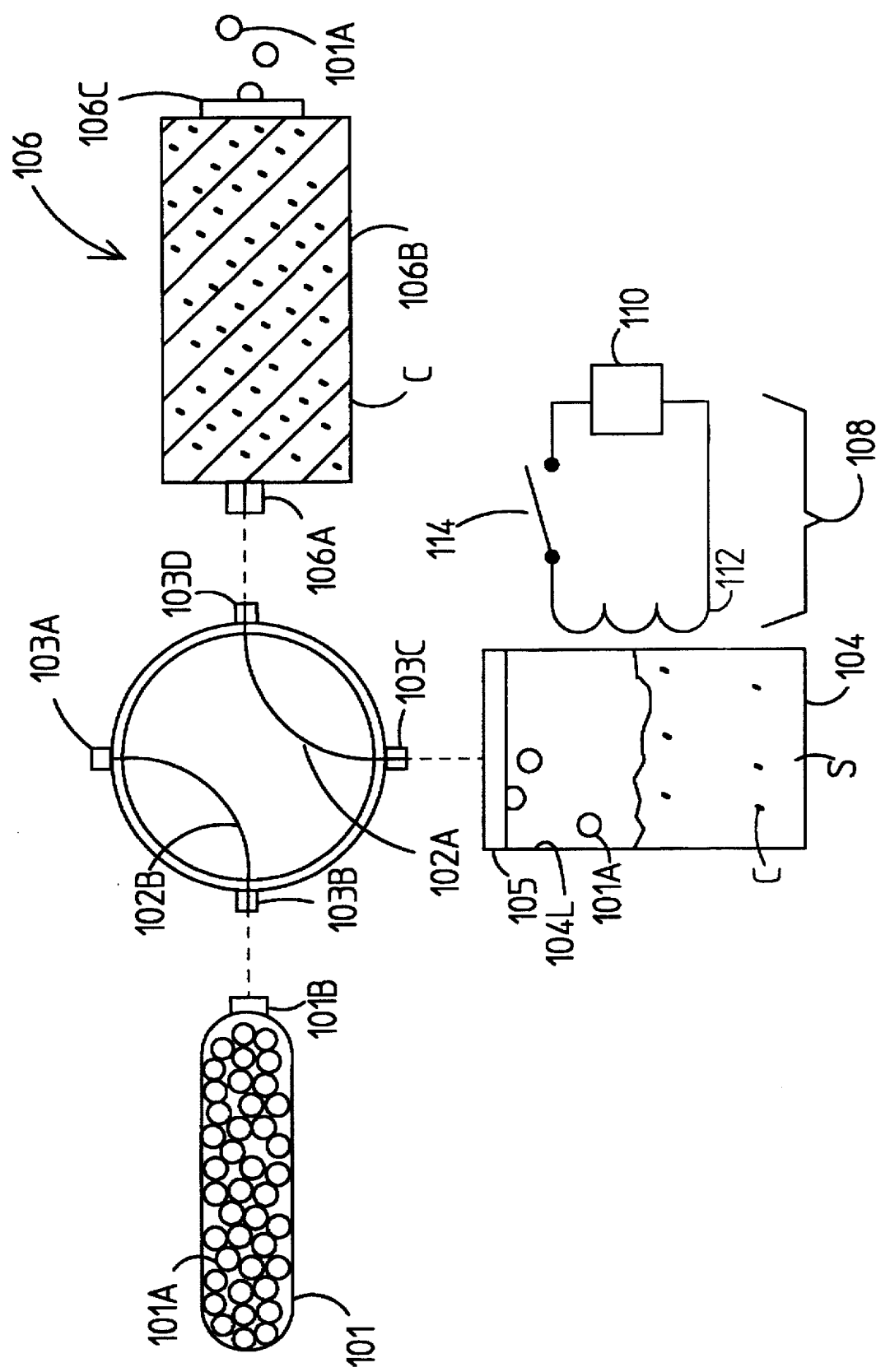
FIG. 4 depicts another simplified schematic representation of the embodiment of FIG. 1 during the completion of the extraction process.

As illustrated in FIG. 4, the valve element 102 is then rotated to a fourth position wherein the first flow path 102A is placed in communication between the sample container 104 and the analyte trap subassembly 106. The second flow path 102B is accordingly positioned in communication between the extraction fluid source 101 and the closed fitting 103. By virtue of the elevated pressure in the sample container 104, a flow of sample/solvent mixture occurs through the cap 105 towards the analyte trap subassembly 106. The flow of the sample/solvent mixture is filtered by the cap 105 such that only the fluid/constituent mixture (comprising pure extraction solvent, mixed extraction solvents, and/or mixtures of analytes dissolved in the extracting solvent) passes through the second flow path 102B. The flow of fluid/constituent mixture encounters a pressure drop in the nozzle 106A. The pressure drop allows splitting of the extracting solvent from the dissolved analytes, since high vapor pressure liquids (such as liquid carbon dioxide or subcritical or near-critical mixtures of fluids such as carbon dioxide plus methanol) expand upon encountering a pressure drop. The nozzle 106A may also be constructed in some applications so as to provide a back pressure regulation function as part of the pressure control of the fluid/constituent flow.

For those fluids which remain liquid upon encountering the pressure drop at the nozzle 106A, the collection trap vessel 106B is situated to vaporize them downstream. The collection trap vessel 106B may be constructed to include a section to baffle the expanding flowing gas stream in which precipitating extracted analytes are entrained. The collection trap vessel 106B is preferably filled with porous or granular material which is either inert or which has some chemical activity, such as adsorbents, or some chemical functionality, such as stationary or bonded liquid phases. The filling or packing used within the collection trap vessel 106B is a parameter which the user may also exploit for fractionation. The preferred packing material may be selected from a group of materials known to exhibit the aforementioned chemical activity or functionality, and such group may include sorbents such as octyl-polysiloxane, octyl-decylsiloxane (ODS), 2,6-diphenylphenylene oxide polymer, and activated charcoal. The output fitting 106C acts as a vent for evaporation or discharge of the extraction fluid.

Figure 5:
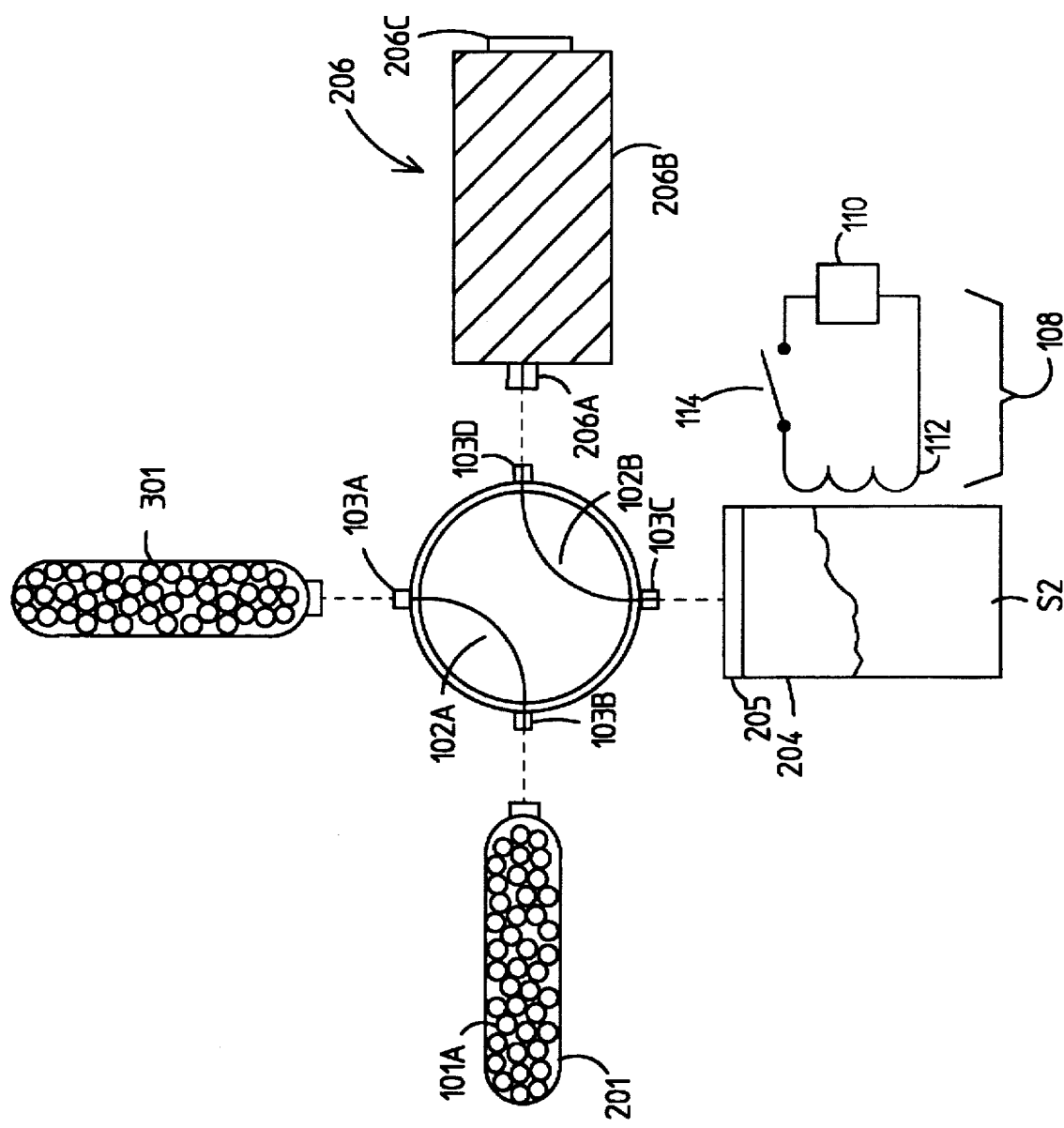
FIG. 5 depicts another simplified schematic representation of the embodiment of FIG. 1 in a condition for effecting another extraction process.

With reference now to FIG. 5, the portable extraction instrument 100 may be seen as partially or wholly reconfigurable such that it is ready for performing another extraction process. Such reconfiguration would include removal or replacement of one or more of the following: the extraction fluid source 101; sample (S), cap 105, sample container 105; and analyte trap subassembly 106. The respective replacements would include: a second extraction fluid source 201; a second sample (S2), a second cap 205, a second sample container 205; and a second analyte trap subassembly 206 (having a second nozzle 106A, a second collection trap vessel 206B, and a second output fitting 206C). The extent and nature of the aforementioned reconfiguration is contemplated as being dependent on the application and the desired outcome, as will now be discussed. The following examples presume that at least one extraction process has been applied to a first quantity of a sample (S) present in the sample container 104, by use of a first solvent in the extraction fluid source 101.

In one example, and subsequent to collection of the analytes in the analyte trap subassembly 106, the analyte trap subassembly 106 is detached from the extraction instrument 100 and retained for later use in, for example, analysis of the extract contained therein. A succession of nozzle/trap subassemblies 106 may be employed to perform a respective series of extractions; each of the nozzle/trap subassemblies are subsequently collected and retained in a suitable container, fixture, or package. Each in the series of extractions may require the replacement of the sample (S) with another quantity of the same sample; for example, the sample (S) is discarded and a second quantity of the same sample is supplied in the sample container 104 for effecting another extraction of the analyte of interest, which is collected in the second nozzle/trap assembly 206. Alternatively, the series of extractions may employ a second sample (S2), a third sample (not shown), and so on. It is a feature of the present invention that such a plurality of nozzle/trap subassemblies 106 are easily detached from the extraction instrument 100 and collected onsite for transport to an analytical instrument situated nearby (e.g., in the field) or at some distance away (e.g., in a traditional laboratory).

Alternatively, by replacing only the extraction fluid source 101, and operating the extraction instrument in a second extraction process, the sample (S) that was previously subjected to the first extraction fluid may then be subjected to a second extraction process using a second, differing extraction fluid that is withdrawn from the second extraction fluid source 201.

In still another example, and as illustrated in FIG. 5, the first sample (S) is removed as raffinate after the first extraction process. The sample container 104, the cap 105, and the analyte trap subassembly 106 are all replaced with a second sample container 204, a second cap 205, and a second analyte trap subassembly 206.

In any of the foregoing extractions, it is contemplated that subsequent to collection of one or more extracts, the collection trap vessel 106B may be removed from the analyte trap subassembly 106 and subjected to solvent desorbtion. Alternatively, the collection trap vessel 106B may be removed and placed in an independently-controlled thermal zone. The collection trap vessel 106B (and accordingly the extract contained therein) may thus be subjected to conditions between sub-ambient and elevated temperatures. For example, the temperature of the collection trap vessel 106B may be increased to a level sufficient to thermally desorb the collected analytes of interest, which would be transported by a gas-like mobile phase at appropriate conditions of pressure, flow rate and identity to analytical instruments, such as gas chromatographs, supercritical fluid chromatographs and liquid chromatographs.

Alternatively, it is contemplated that additional apparatus may be attached to the output fitting 106C to effect additional sample preparation or analytical processes during (or subsequent to) the extractions described hereinabove. For example, fractionation in the region downstream of the collection trap vessel 106B may employ the wealth of stationary phases found to provide specificity in the fields of analytical and preparative scale chromatography (e.g., gas-liquid and gas-solid chromatography, normal and reversed phase liquid chromatography, normal and reversed phase thin layer chromatography, adsorption chromatography, supercritical fluid chromatography, size exclusion chromatography). Thus, in certain embodiments, the apparatus described herein can superimpose chromatographic-like selectivity due to stationary phase interaction on the fractionating capability inherent in a supercritical fluid extraction device for clean-up of samples in the analytical lab.

In certain embodiments of the present invention, the valve element 102 may be operated to permit the portable extraction instrument 100 to be configured and operated to overcome problems encountered during extraction. Such problems include the occlusion of one or more of the fluid paths of the portable extraction instrument 100 and the region directly downstream from the restrictors that are used to maintain system pressure by providing a pressure drop (e.g., the nozzle 106A). The occlusion occurs as a result of the precipitation of dissolved analytes in the flow stream, the extrusion of melted matrix or matrix components into the flow stream, particulates from the sample that are too small to be captured in the filter in the cap 105, or the erosion of particles from the portable extraction instrument itself, such as metal filings and polymeric particulates from sealing materials, and the subsequent accumulation of such particulate matter.

In the rinsing methods of the present invention, the valve element may be set to deliver a quantity of extraction fluid at an appropriate pressure and flow rate to an empty sample container 104. The valve element 102 may then be set to allow extraction fluid flow from the sample container 104 through the valve element 102 and the analyte trap subassembly 106. Such rinsing methods may be employed to dislodge and transport insoluble particulate matter in the ports 103, first or second fluid flow paths 102A, 102B, or the throat section of the nozzle 106A. Alternatively, extraction fluid may delivered at an appropriate pressure, flow rate, and solvent power so as to dissolve deposited, precipitated, or adsorbed components and transport the resulting solution through the throat of the nozzle 106A to an expansion region such as the collection trap vessel 106B. Finally, such rinsing method concludes with the step of restoring the setting of the valve element 102 so that the extraction fluid source 101 is isolated.

For example, it is contemplated that the extraction instrument 100 may be flushed by attaching an empty sample container 104 and rotating the valve element 102 through various positions so as to provide one or more quantities of extraction fluid 101A serially through the several parts of the extraction instrument 100. This method dissolves unwanted residual components and moves them to a collection trap vessel 106B that has been attached solely for collection of the unwanted residual components. The present invention also contemplates the removal of deposited components by flushing the extraction instrument with a particular formulation of extraction fluid. Accordingly, a particular extraction fluid source 101 may be reserved expressly for rinsing or cleaning and would contain a particularly effective solvent fluid, e.g., pressurized liquids such as organic solvent systems, acids, bases, aqueous solvent systems; or sub-, near- and supercritical fluids including mixtures.

When rinsing or flushing steps are completed, the analyte trap subassembly 106 or merely the collection trap vessel 106B is then removed for disposal and a new version of the disposed piece is substituted.

In other embodiments of the present invention, it may be desirable to incorporate more than one analyte trap subassembly 106 in the extraction instrument 100. Such additional nozzle/trap subassemblies 106 would either be incorporated onto the fourth valve element port 103D or resident on other instruments coupled thereto. For example, a ganged (plural) array of the analyte trap subassembly 106 may be the only subassembly attached to the fourth valve element port 103D. In other embodiments, comparable nozzle and/or trap subassemblies resident on other instruments may be substituted entirely for those preferably provided as a part of the analyte trap subassembly 106 made in accordance with the present invention.

Similarly, in still other embodiments of the present invention, it may be desirable to incorporate more than one sample container 104 in the extraction instrument 100. Such additional sample containers 104 would either be incorporated with respective caps 105 onto the third valve element port 103C, or may be modified for attachment onto a single cap 105. For example, a ganged (plural) array of sample containers 104 and caps 105 may be fitted onto to the third valve element port 103C.

It is also contemplated that the sample container 104 may be constructed to employ a replaceable, disposable inner liner 104L, such that one sample container 104 may be reused by insertion of a new liner 104L. The liner 104L may thus be constructed to be especially inexpensive and inert (i.e., not chemically reactive) and the sample container 104 may be constructed to be especially strong and lightweight.

In still other embodiments of the present invention, it may be desirable to attach more than one extraction fluid source 101 to the extraction instrument 100. As illustrated in FIG. 5, an additional extraction fluid source may be incorporated as a third extraction fluid source 301 onto to the first valve element port 103A. Alternatively, still more extraction fluid sources may be incorporated as a ganged (plural) array of extraction fluid sources 101 that are fitted onto to the second valve element port 103B.

Another modification to the apparatus of the present invention is the modification of the output fitting 106C so as to provide a fluid connection between the output fitting 106C and an analytical instrument—e.g., a liquid chromatograph, UV/VIS spectrophotometer, or liquid sampler—such that a fraction rinsed or otherwise not completely trapped by the analyte trap subassembly 106 can be directed to the analytical instrument for further manipulation and subsequent analysis. Such a modification thus contemplates either: a) the attachment of the analytical instrument to the output fitting 106C for operation of the analytical instrument while the analyte trap subassembly is installed on the extraction instrument 100; or, the analyte trap subassembly 106 may be detached from the extraction instrument 100 and subsequently attached to the analytical instrument.

Such analytical apparatus can provide sampling of the extraction fluid vented from the output firing 106C subsequent to recovery of solutes in the analyte trap subassembly 214 or prior to being directed to other instruments. For example, the sampled stream may be directed to a UV/VIS spectrophotometer or through sampling valves on a variety of other analytical instruments such as liquid chromatographs, supercritical fluid chromatographs, and gas chromatographs.

As set forth above, the collection trap vessel 106B is preferably filled with a chemically-active packing material. Alternate embodiments of the collection trap vessel 106B may include additional materials, structures, or plural regions containing differing types of chemically active packing material and other porous material. In terms of the present invention, any of the physical or chemical characteristics which contribute to some degree of selectivity of movement among various migrating spades exposed to that stationary phase media are defined as "chemically active." One may choose stationary phases to have selective interaction with various molecules which come into contact with the stationary phase. When the motion of a mobile phase can move molecules relative to a stationary phase, the selective interaction can result in separations of different compounds.

Typical mobile phases are liquids, gases, and supercritical fluids. Stationary phases can be supported as films or layers on a surface (e.g., thin layer chromatography, open tubular or capillary column chromatography) or on particles with which fluids can come in contact. Thus, even the surfaces may be considered to be the stationary phase, possibly having been modified for chemical activity, functionality, or size selectivity, e.g., bonded phase chemistry, adsorption chemistry, and chiral interactions.

It is also contemplated to exploit the physical dimensions of the stationary phase to maximize selectivity, for example with respect to the chosen mobile phase characteristics (van Deemter and Golay equations), or with respect to the diffusion time through liquid layers and within pores, or with respect to the spatial geometry (overall size and shape) of the migrating compounds. The last example is more relevant to particles making up the stationary phase. In some cases, the selectivity may be extreme, some or all of the species migrating with a bulk mobile or carrier phase are substantially irreversibly removed from the mobile phase and retained by the stationary phases.

In certain embodiments of the present invention, the extraction fluid source 101, sample container 104, cap 105, and analyte trap subassembly 106 as described above may be supplemented with additional useful features or characteristics, such as the provision of: identification means (e.g., a colored exterior, a surface for receiving handwritten notations, or a label such as a bar-coded label); thermal insulation (e.g., a foam jacket); a shape or configuration consistent with the intended use in the extraction process (e.g., an aperture having a particular shape or thread, or locking device, that allows the particular item to be installed only on a particular one of the ports 103); or a shape or configuration consistent with a pre- or post-extraction use (e.g., ridges for gripping by the hand; or, in the case of the collection trap vessel, a shape compatible for use as an autosampler vial in an autosampling apparatus.)

The engineering of the portable extraction instrument of the present invention applies an understanding of the important parameters and limitations in the areas of supercritical fluid extraction, (supersonic) expansion of fluids, the collection/reconstitution of extract, and passive (i.e. without use of pumping apparatus) transport of compressible fluids. The present invention also provides a method for operating a fluid extraction system without need for complex pressure control systems or thermal control systems.

As set forth above, the preferred embodiments utilize a pressurized extraction fluid in lieu of pumping apparatus for effecting extraction fluid transport. In certain embodiments, the selection of the composition of the extraction fluid is provided by selecting a specific extraction fluid source. The design of the present invention also provides for effecting thermal/pressure control of the sample/solvent mixture, particularly for effecting the critical, near-critical, and super-critical conditions that can enhance extraction. In one preferred embodiment, a heating unit may be utilized to effect the requisite pressure-volume-temperature conditions, thus allowing density to be input as the relevant parameter for solvent power. Further, the contemplated extraction instrument permits rinsing and/or flushing of the analyte to occur.

The apparatus and methods disclosed herein allow the user to focus on the significant task of collecting large number of samples and performing a large number of the requisite extractions in a simple, efficient, and speedy fashion. The operator thus avoids having to use extensive equipment and time-consuming methods. The present invention especially useful in non-traditional settings (e.g., in the field, and in adverse environments as well as in traditional settings (e.g. the laboratory).

Although certain embodiments of the present invention have been set forth with particularity, the present invention is not limited to the embodiments disclosed. Accordingly, reference should be made to the appended claims in order to ascertain the scope of the present invention.

What is claimed is:

1. A method for effecting extraction of an analyte from a sample, comprising the steps of:
   (1) providing an extraction instrument comprising a sample container for retaining the sample, an extraction fluid source for providing pressurized extraction fluid at a pressure above atmospheric pressure, an analyte trap subassembly including a collection trap vessel, and a valve element having ports thereon for respective attachment of the sample container, extraction fluid source, and analyte trap subassembly;
   (2) inserting a sample in the sample container and attaching the sample container to the valve element;
   (3) providing a quantity of extraction fluid from the extraction fluid source through a first flow path in the valve element into the sample container, to cause the extraction fluid and sample to mix and form a sample/solvent mixture;
   (4) arresting the extraction fluid flow and initiating a selectable time period for achieving extraction of one or more constituents of interest, thus providing a fluid/constituent mixture; and
   (5) directing the fluid/constituent mixture through a second flow path in the valve element from the sample container into the analyte trap subassembly whereby the analyte of interest present in the fluid/constituent mixture is trapped in the collection trap vessel.

2. The method of claim 1, further comprising the step of inducing an elevated temperature in the sample/fluid mixture while the sample/fluid mixture is contained in the sample container so as to cause the sample/fluid mixture to achieve a supercritical condition and thereby facilitate extraction of the analyte.

3. The method of claim 1, wherein the extraction fluid is a solvent and the extraction achieved in at least one of steps (3)–(4) includes solvation of the analyte of interest.

4. The method of claim 1, wherein the extraction fluid is a volatile fluid and the extraction achieved in at least one of steps (3)–(4) includes volatilization of the analyte of interest.

* * * * *